United States Patent [19]

Ho

[11] 4,284,784
[45] Aug. 18, 1981

[54] PROCESS FOR THE PREPARATION OF 4-METHYL THIAZOLE

[75] Inventor: Sa V. Ho, St. Louis, Mo.

[73] Assignee: Merck & Co., Inc., Rahway, N.J.

[21] Appl. No.: 152,282

[22] Filed: May 22, 1980

[51] Int. Cl.$^3$ .................................................. C07D 277/20
[52] U.S. Cl. .................................... 548/202; 548/146; 424/270
[58] Field of Search ................ 548/146, 202; 424/270

[56] References Cited

U.S. PATENT DOCUMENTS

| 3,284,536 | 11/1966 | Bajars et al. | 260/683.3 |
| 3,308,182 | 3/1967 | Gabliks et al. | 260/680 |
| 3,649,560 | 3/1972 | Croce et al. | 252/432 |
| 3,666,687 | 5/1972 | Croce et al. | 252/439 |

OTHER PUBLICATIONS

Adams, Jour. of Catalysis II, pp. 96–112 (1968.
Colebourne et al., J. Chem., pp. 685–688 (1968).

*Primary Examiner*—Nicholas S. Rizzo
*Attorney, Agent, or Firm*—David L. Rose

[57] ABSTRACT

An improved process for the preparation of 4-methyl thiazole is disclosed. The process utilizes a substituted imine and sulfur dioxide heated in the presence of a catalyst. The thiazoles are known important chemical intermediates.

16 Claims, No Drawings

PROCESS FOR THE PREPARATION OF 4-METHYL THIAZOLE

BACKGROUND OF THE INVENTION

Many processes have been disclosed for the preparation of thiazoles owing to the importance of such compounds as chemical intermediates. One such process disclosed by Colebourne (*Journal of the Chemical Society* 685 (1967) involves an imine in the presence of sulfur to prepare 4-methylthiazole. The process has the distinct disadvantage of having hydrogen sulfide, an environmental pollutant, as a by product.

SUMMARY OF THE INVENTION

The instant invention prepares thiazole compounds from an imine and sulfur dioxide, avoiding the production of the hazardous by-product, hydrogen sulfide. Thus, it is an object of this invention to describe the preparation of 4-methyl thiazole from an imine and sulfur dioxide. Another object of this invention is to describe the catalyst which may be used in such process. Still another object of this invention is to describe the reaction conditions which allow the process to be carried out in a continuous fashion. Further objects will become apparent upon reading the following description.

DESCRIPTION OF THE INVENTION

The process of the instant invention is best described in the following reaction scheme:

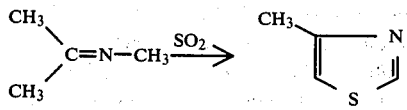

The process for the instant reaction involves the reaction of the appropriately substituted imine (I) with sulfur dioxide in the presence of a catalyst. The reaction is carried out in the vapor phase at elevated temperatures.

In practice, a stream of a mixture of the imine and sulfur dioxide in an inert carrier gas, preferably nitrogen, is passed over the catalyst maintained at a temperature of from 400°-500° C. The preferred temperature is from 420°-460° C., with the preferred temperature for the preferred product being about 440° C.

Generally, about equal molar amounts of sulfur dioxide and the imine are employed, however, an excess of up to 10 moles of one component over the other may be employed. However, since any unreacted sulfur dioxide may be recovered from the reaction mixture and recycled, and the imine cannot be, since unreacted imine is degraded in the reactor, the use of excess imine is not economically desireable and not preferred. A slight excess of sulfur dioxide to reduce the production of imine degradation products is most preferred.

Generally, the imine is present in the reaction stream from about 3 to 5 mole percent. The sulfur dioxide is present from about 3.6 to 10 mole percent. It is most preferred to use about 3.65 mole percent of the imine and about 5.1 mole percent of sulfur dioxide.

The catalyst for the instant process is a two part (binary) or three part (ternary) metal oxide mixture wherein a mixture the oxides of two or three metals, one of which is iron is employed. The other metals may be any metals other than the alkali metals, however, it is preferred that they be selected from the alkaline earth metals, transition metals and the metal of Groups IIIa and IVa of the Periodic Table. In all cases, the oxides of the metals are used. The particular oxide of a metal used in the catalyst is not determined and in fact a single metal may be present in the catalyst in more than one oxidation state.

The composition of the catalyst is defined in terms of the ratios by weight of each of the metals present, as set forth in the following formula:

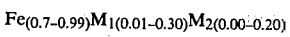

wherein $M_1$ and $M_2$ are metals other than alkali metals, and in particular are selected from the alkaline earth metals, transition metals, and Groups IIIa and IVa metals. The parenthetical numbers indicate the ratio of the metal found in the catalyst relative to the total metal content of such catalyst. That is iron is present in from 70 to 99%, $M_1$ from 1 to 30% and $M_2$ from 0 to 20 percent.

The preferred metals for $M_1$ and $M_2$ are those alkaline earth, transition and Groups IIIa and IVa metals with an atomic number less than 57. Examples of such preferred metals are aluminum, chromium, magnesium, tin, zinc, zirconium and lanthanum. The most preferred metals are aluminum, chromium and zinc.

The preferred catalyst is a ternary catalyst wherein the iron is present at from 80 to 90%, $M_1$ is present at from 5 to 15% and $M_2$ is present at from 1 to 5%. The most preferred catalyst utilize oxides of iron, aluminum and chromium wherein the metals are present in the following approximate amounts: iron 86.7%, aluminum 10.2% and chromium 3.1%.

The catalyst may be supported or unsupported, however, since the catalyst is stable and non-fusible at the temperature employed, and to insure a longer operating life between catalyst regenerations, the catalyst is preferred to be unsupported. The contact time for the reaction mixture is generally maintained at from 2-8 seconds to insure maximum reaction of the reagents and yield of the product.

The size of the reaction vessel and the amount of catalyst present is immaterial to the instant process, since larger vessels and more catalyst merely provides for a longer useful life of the catalyst before regeneration is required.

The catalyst is reusable, however, during the reaction a coating of "coke" or carbonaceous deposits is formed on the catalyst which presumably is a degradation product or products from the decomposition of a small amount of the imine starting materials. The catalyst is regenerated by passing air, at reaction temperatures (400°-500° C.) over the catalyst for from 2-10 hours.

The product of the instant process is recovered generally by cooling the reaction mixture gas and vapor stream from the reactor to ambient temperatures. The thiazole condenses and is recoverable and the nitrogen carrier gas and any unreacted sulfur dioxide may be scrubbed of any imine degradation products and recycled into the reactor after being supplemented with additional sulfur dioxide and imine. It is also possible to cool the reactor effluent by passing it through water or an aqueous acid solution to disolve the thiazole. The thiazole may then be recovered from the water or aqueous acid by conventional means.

The catalyst is prepared by dissolving salts of the metal oxides desired into water. A salt which will readily dissolve and which will leave no residue on calcination is preferred and thus nitrate salts are preferred. After the salts are dissolved in water, the water is evaporated to dryness. Thorough drying, such as in air at about 200° C. is preferred to ensure that all traces of water are removed. The dried mixture of salts is then calcined at about 600° C. for from 12 to 16 hours. The calcining process decomposes the salts, in the case of nitrate salts by releasing nitrogen dioxide gas, leaving a residue of a mixture of metal oxides. The mixture is then pulverized and granulated to the desired mesh size for use in the reactor. The particle size of the catalyst is controlled by passing the granulated catalyst through a graduated series of sieves. The preferred particle size for the instant catalyst is from 18 to 39 mesh. The final concentration of the mixture of metal oxides is determined by the molar ratios of the metal cation of the salts that are initially dissolved in the water.

The imine starting material is a known compound which is prepared by reacting acetone with methylamine as shown in the following reaction:

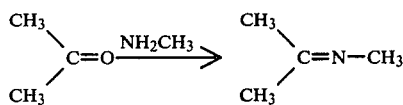

The reactants are heated together at a temperature of from 20° to 100° C. for from 2 to 20 hours either with or without an inert solvent such as toluene, benzene, and the like. The water by product is removed during the course of the reaction to force it to completion and the product is isolated using techniques known to those skilled in the art.

As noted above, the instant reaction produces the instant thiazole compounds without any polluting by-products. Prior processes resulted in the liberation of hydrogen sulfide which, if released to the atmosphere, presented a considerable environmental hazard; and if recovered, presented extra expenses in the recovery process and safe disposal. The only products prepared in the instant process are 4-methyl thiazole and water. Any excess sulfur dioxide unreacted in passing through the reactor is recycled back into the inlet of the reactor. Thus, the instant process presents a considerable advantage over prior processes for the preparation of thiazoles.

The 4-methyl thiazole prepared by the process of this invention is a useful industrial chemical which may be an intermediate for the preparation of other industrially and biologically active compounds. The compound, in particular is a valuable intermediate in the preparation of thiabendazole, an important anthelmintic agent for the treatment of gastrointestinal parasites in mammals, and also an important industrial and agricultural fungicide.

The following examples are provided in order that the invention might be more fully understood. They are not meant to be limitative of the invention.

EXAMPLE 1

A metal oxide catalyst mixture is prepared by dissolving the following salts in about 0.5 liter of water:
7.5 g (0.02 moles) of Al(NO$_3$)$_3$.9H$_2$O
2.38 g (0.006 moles) of Cr(NO$_2$)$_3$.9H$_2$O
68.66 g (0.17 moles) of Fe(NO$_3$)$_3$.9H$_2$O The resulting solution is evaporated to dryness in a porcelain dish, then air dried at 200° C. The residue is then calcined at 600° C. overnight. The calcined mass is ground lightly, screened and the fraction retained at 18-30 mesh.

23 G of the 18-30 mesh catalyst mixture is loaded into a microreactor core consisting of a heated metal cylinder with a ¼ inch lengthwise hole therethrough. A thermocouple is placed in a 1/16 inch diameter tube along the axis of the bar. Nitrogen is passed over the catalyst and the reactor heated to the desired temperature of 440° C.

The imine is introduced into the nitrogen stream through a carburator which is controlled by a thermostat so as to afford a saturated gas stream of the desired concentration 3.65% by volume. Sulfur dioxide is introduced into the nitrogen stream just prior to entering the gas preheating zone, at a rate that provides the desired concentration in the total mixture of 5.1% by volume. The total gas rate is 100 ml per minute over the 2.3 g of catalyst.

Gas samples are taken from both the inlet and outlet of the reactor and analyzed by gas chromatography for imine and 4-methylthiazole. This permits the determination of the rate of imine conversion, the 4-methylthiazole yield and the reaction selectivity.

The percent yield is obtained by dividing the amount of 4-methylthiazole produced by the imine feed (times 100).

The percent selectivity is obtained by dividing the amount of 4-methylthiazole produced by the amount of imine consumed (times 100).

The calculation of the above percentage at various intervals during the course of the reaction causes the observation of 3 distinct phases in the process:

(A) Induction Period—40 minutes in duration, 100% imine conversion throughout; percent yield of 4-methylthiazole increases linearly from 0 to 50%.

(B) Production Period—120 minutes in duration, 100% imine conversion throughout; percent yield of 4-methylthiazole increases from 50 to 59–60%.

(C) Decay Period—Imine percent conversion decayed from 100 to 65% over 100 minutes; percent yield of 4-methylthiazole decayed accordingly (at a constant selectivity of 60%/from 59–60% to 39%.

The gas flow can then be stopped and the catalyst regenerated by heating in a stream of air at 450° C. for several hours. The process may then be restarted.

EXAMPLE 2

A binary catalyst prepared from 72.7 g (0.18 moles) of Fe(NO$_3$)$_3$.9H$_2$O and 4.76 g (0.02 moles) of Cr(NO$_3$)$_3$.9H$_2$O using the process of Example 1, except that the calcining temperature is 690° C.

The catalyst is pulverized to 18-30 mesh and 2.5 g is placed in a microreactor. The reaction is carried out with an imine feed concentration of 3.9% and a sulfur dioxide concentration of 5.0% and a total gas flow rate of 96.3 ml per minutes. The reaction has a maximum selectivity of 57%.

What is claimed is:

1. A process for the preparation of 4-methylthiazole which comprises reacting an imine having the formula:

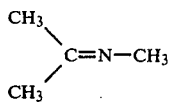

with sulfur dioxide in the presence of a catalyst consisting of a mixture of oxides of iron and one or two of the oxides of metals selected from alkaline earth metals, transition metals, and the Group IIIa and IVa metals of the periodic table.

2. The process of claim 1 wherein the catalyst is a mixture of oxides of iron and one or two of alkaline earth, transition and Group IIIa and IVa metals with an atomic number less than 57.

3. The process of claim 2 wherein the catalyst is a mixture of oxides of iron and one or two of aluminum, chromium, magnesium, tin zinc, zirconium and lanthanum.

4. The process of claim 3 wherein the catalyst is a mixture of oxides of iron and one or two of aluminum, chromium and zinc.

5. The process of claim 1 wherein the catalyst is a ternary catalyst.

6. The process of claim 1 wherein the catalyst consists of oxides of iron and one or two additional metals such that the iron is present at from 70 to 99% the first additional metal is present at from 1 to 30% and the second additional metal is present at from 0 to 20%.

7. The process of claim 6 wherein the metal oxides are present at from 80 to 90% of iron, from 5 to 15% of the first additional metal and from 1 to 5% of the second additional metal.

8. The process of claim 7 wherein the catalyst consists of metal oxides of iron, aluminum and chromium.

9. The process of claim 8 wherein the catalyst consists of metal oxides such that iron is present at about 86.7%, aluminum at about 10.2% and chromium at about 3.1%.

10. The process of claim 1 wherein the reaction is maintained at a temperature of from 400°–500° C.

11. The process of claim 10 wherein the reaction is maintained at a temperature of from 420°–460° C.

12. The process of claim 11 wherein the reaction is maintained at a temperature of about 440° C.

13. The process of claim 1 wherein from 10 moles of the imine is used for each mole of sulfur dioxide, to 1 mole of the imine for 10 moles of sulfur dioxide.

14. The process of claim 1 wherein substantially equimolar amounts of the imine and sulfur dioxide are used.

15. The process of claim 1 wherein the imine is present in the reaction stream at about 3–15 mole percent and sulfur dioxide is present at from about 3.6 to 10 mole percent.

16. The process of claim 15 wherein the imine is present in the reaction stream at about 3.6 mole percent and the sulfur dioxide is present at about 5.1 mole percent.

* * * * *